(12) United States Patent
Van De Bunt

(10) Patent No.: US 12,324,399 B2
(45) Date of Patent: Jun. 10, 2025

(54) GARDEN BEAN VARIETY 'LUNAR'

(71) Applicant: KWS VEGETABLES BV, Gelderland (NL)

(72) Inventor: Gerthon Van De Bunt, Andijk (NL)

(73) Assignee: KWS VEGETABLES B.V., Gelderland (NL)

(*) Notice: Subject to any disclaimer, the term of this patent is extended or adjusted under 35 U.S.C. 154(b) by 303 days.

(21) Appl. No.: 18/051,760

(22) Filed: Nov. 1, 2022

(65) Prior Publication Data
US 2024/0138358 A1  May 2, 2024

(51) Int. Cl.
A01H 6/54 (2018.01)
A01H 5/10 (2018.01)

(52) U.S. Cl.
CPC ............ A01H 6/545 (2018.05); A01H 5/10 (2013.01)

(58) Field of Classification Search
None
See application file for complete search history.

(56) References Cited

U.S. PATENT DOCUMENTS 10,390,514 B2  8/2019  Van De Bunt
10,561,110 B1 * 2/2020  Van De Bunt ........... A01H 5/08

OTHER PUBLICATIONS

Oxford Dictionary Online, definition: significantly (2024) downloaded on Nov. 16, 2024 from https://www.google.com/search?q=definition+significantly (Year: 2024).*
U.S. Appl. No. 17/820,965, filed Aug. 19, 2022, 25 pages.
U.S. Appl. No. 18/046,543, filed Oct. 14, 2022, 26 pages.

* cited by examiner

Primary Examiner — Cathy Kingdon
(74) Attorney, Agent, or Firm — McKee, Voorhees & Sease, PLC

(57) ABSTRACT

A new variety of garden bean (*Phaseolus vulgaris* L.) designated 'Lunar' is provided. Garden bean variety 'Lunar' is characterized by its dark green pods in mainly the 4 sieve class, heat tolerance, strong, compact and erect plant habit, and resistance to several races of *Colletotrichum lindemuthianum* (Anthracnose) and *Uromyces appendiculatus* (Rust).

24 Claims, 3 Drawing Sheets
(3 of 3 Drawing Sheet(s) Filed in Color)

GARDEN BEAN VARIETY 'LUNAR'

FIELD

This disclosure relates to the field of plant breeding. In particular, this disclosure relates to a new and distinctive garden bean, *Phaseolus vulgaris* L., designated 'Lunar'.

BACKGROUND

Cultivated forms of garden bean belong to the highly variable species *Phaseolus vulgaris* L. that is commonly grown for its seeds (beans) and fruits (pods), which are harvested together as an immature pod before the seeds have fully matured. This immature pod is known by many different names, including common bean, green bean, string bean, snap bean, French bean, haricot bean, and filet bean. As a crop, garden bean is grown commercially wherever environmental conditions permit the production of an economically viable yield. Bean cultivars may be grouped by their growth habit into two groups. Bush or dwarf cultivars grow as erect bushes or short vines, do not require support, and are commonly grown on commercial farms. Pole, climbing, or running cultivars grow as long vines that climb supports, and are commonly grown in home vegetable gardens. The size of garden bean pods ranges from small to large, and from narrow, round French types to wide, flat Roma types. More recent developments in garden bean breeding have led to a wider array of fruit color. In addition to the standard green color, pods can be purple, red, yellow, or mottled. Garden beans are consumed fresh or cooked, and can be sold in fresh, frozen, dried, or canned form.

*Phaseolus* is a genus within the family Fabaceae and consists of about 70 species. Fabaceae (or Leguminosae) is one of the largest land plant families, with an estimated 19,000 species, and contains multiple crop species including lentil, chickpea, soybean, bean, pea, peanut, and alfalfa. The leguminous plants of this family are characterized by their symbiosis with *Rhizobium* bacteria, which fix atmospheric nitrogen that is eventually released into the soil. Legumes are therefore often used to increase the nitrogen content of soil, and frequently grown either in rotation or concurrently with other crops. One example of this is found in indigenous North American agriculture, where beans are a member of the "Three Sisters" and are planted with squash and maize.

*Phaseolus vulgaris* L. is a highly variable species with a wide diversity of phenotypes. *P. vulgaris* L. is native to the Americas. and has a long history of cultivation dating from the second millennium BCE and spanning South and North America. There are three broad types of bean cultivars, namely dry bean, shelling bean, and green bean. Two separate domestication events from two genetically distinct wild populations in Middle America and the Andes resulted in two distinct gene pools among bean cultivars (Gepts, *HortScience*. 33:7, 1124-1130, 1998). These two gene pools can be distinguished using phenotypic and genetic characteristics, and each provides qualities useful in developing new bean cultivars. Each gene pool has been used to develop different commercial seed classes; in the Andean gene pool, the Nueva Granada race includes kidney beans and green beans, while in the Middle America pool, the Mesoamerican race includes navy and black beans and the Durango race includes pinto beans.

Garden bean is an important and valuable crop. Thus, there is a continued need for new garden bean varieties. In particular, there is a need for improved garden bean varieties that are stable, high yielding, and agronomically sound.

SUMMARY

In order to meet this need, the present disclosure provides an improved garden bean (*Phaseolus vulgaris* L.) variety 'Lunar' (Breeder's designation 'PV-959'). In one embodiment, the present disclosure provides a seed of garden bean variety designated 'Lunar', wherein a representative sample of seed of the variety has been deposited under NCIMB Accession No. 44005. In another embodiment, the present disclosure provides a garden bean plant produced by growing the seed. Also provided is a garden bean plant having all of the physiological and morphological characteristics of garden bean variety designated 'Lunar'. In a further embodiment, the present disclosure provides a garden bean plant which does not significantly differ from the garden bean variety designated 'Lunar' (i e when evaluated at significance levels of 1%, 5%, or 10% significance, which can also be expressed as p value).

In a further embodiment, the present disclosure provides a plant part from the garden bean plant, which in some embodiments is a leaf, a pod, a garden bean hull, a garden bean, a stem, a root, or a flower. Additionally, the present disclosure provides a tissue culture of regenerable cells produced from a plant part selected from the group consisting of embryos, meristematic cells, leaves, pollen, roots, root tips, stems, anthers, pistils, pods, flowers, and seeds. Moreover, a garden bean plant regenerated from the tissue culture is provided, wherein the plant has all of the physiological and morphological characteristics of garden bean variety 'Lunar' when evaluated at significance levels of 1%, 5%, or 10% significance.

The present disclosure is also directed to a method for producing a hybrid garden bean seed, comprising crossing a first parent garden bean plant with a second parent garden bean plant and harvesting the resultant hybrid garden bean seed, wherein the first parent garden bean plant or the second parent garden bean plant is the plant of the preceding paragraph. In some embodiments, the present disclosure provides a hybrid garden bean seed produced by the method, as well as a garden bean plant produced by growing the seed, and a plant part isolated from the plant.

In addition, the present disclosure is directed to a method for producing a transgenic garden bean plant, comprising transforming the plant of the preceding paragraphs with a transgene that confers a trait. In some embodiments, the trait is selected from the group consisting of herbicide resistance, insect resistance, disease resistance, and a combination thereof. In a subset of these embodiments, the trait is herbicide resistance and the herbicide is selected from the group consisting of imidazolinone, sulfonylurea, glyphosate, glufosinate, L-phosphinothricin, triazine, and benzonitrile. In another embodiment, the trait is insect resistance and the insect resistance is conferred by a transgene encoding a *Bacillus thuringiensis* endotoxin. In some embodiments, the present disclosure provides a transgenic garden bean plant, or a plant part thereof, produced by the method.

Furthermore, the present disclosure is directed to a method for introducing a trait into garden bean variety 'Lunar', the method comprising: (a) crossing a plant of garden bean variety 'Lunar', wherein a representative sample of seed of the variety has been deposited under NCIMB Accession No. 44005, with another garden bean plant that comprises a trait to produce $F_1$ progeny plants, wherein the trait is selected from the group consisting of insect resistance, disease resistance, water stress tolerance, heat tolerance, improved shelf-life, improved nutritional quality, improved yield, and a combination thereof; (b) selecting one or more progeny plants that have the trait to produce selected progeny plants; (c) backcrossing the selected progeny plants with plants of garden bean variety 'Lunar' to produce backcross progeny plants; (d) selecting for backcross progeny plants that have the trait; and (e) repeating steps (c) and (d) one or more times to produce further backcross progeny plants that have the trait. In some embodiments, the trait is herbicide resistance and the herbicide is selected from the group consisting of imidazolinone, sulfonylurea, glyphosate, glufosinate, L-phosphinothricin, triazine, and benzonitrile. In another embodiment, the trait is insect resistance and the insect resistance is conferred by a transgene encoding a *Bacillus thuringiensis* endotoxin. In some embodiments, the present disclosure provides a garden bean plant, or a plant part thereof, produced by the method, wherein the plant has the trait and otherwise has all of the physiological and morphological characteristics of garden bean variety 'Lunar' when evaluated at significance levels of 1%, 5%, or 10% significance.

Also, the present disclosure is directed to a method for producing a garden bean pod, comprising (a) cultivating the plant of the preceding paragraphs to produce a garden bean pod; and (b) harvesting the garden bean pod. Moreover, the garden bean pod produced by the method is provided.

In another aspect, the present disclosure is directed to a method of producing a garden bean plant derived from 'Lunar', the method comprising the steps of: (a) preparing a progeny plant derived from 'Lunar', wherein said preparing comprises crossing a plant of the garden bean variety 'Lunar' with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from garden bean variety 'Lunar'. The plant derived from garden bean variety 'Lunar' may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from garden bean variety 'Lunar' is obtained which possesses some of the desirable traits of the variety as well as potentially other selected traits.

BRIEF DESCRIPTION OF THE DRAWINGS

The patent or application file contains at least one drawing executed in color. Copies of this patent or patent application publication with color drawings will be provided by the office upon request and payment of the necessary fee.

The accompanying photographs illustrate the overall appearance of the new garden bean variety 'Lunar' (Breeder's designation 'PV-959'), showing the colors as true as is reasonably possible with colored reproductions of this type. The comparative garden bean variety is 'PV-857' (U.S. Pat. No. 10,390,514)

DETAILED DESCRIPTION

Figure 1:
FIG. 1 is a photograph of plants of garden bean variety 'Lunar' with pods.
Figure 2:
FIG. 2 is a photograph of pods of garden bean variety 'Lunar'.
Figure 3:
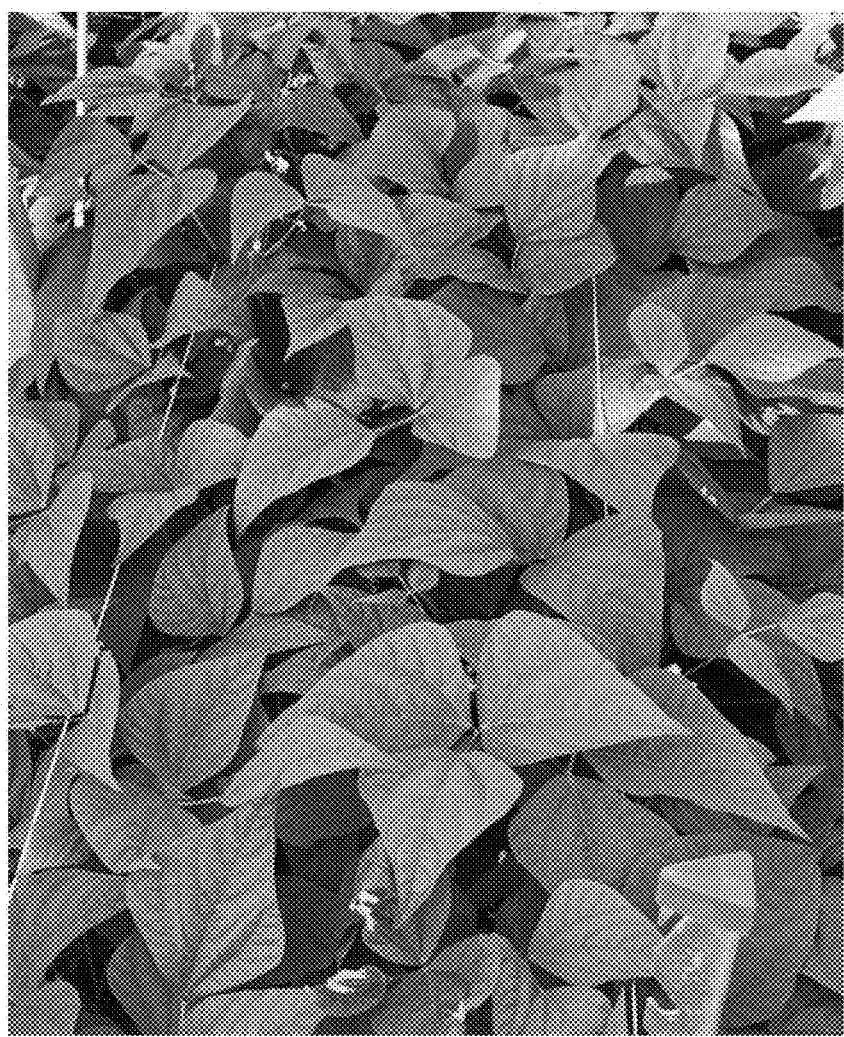
FIG. 3 is a photograph of a top view of garden bean variety 'Lunar'.

The disclosure provides compositions and methods relating to seeds, plants and plant parts of a novel garden bean variety designated 'Lunar'.

I. Definitions

In the description and tables that follow, a number of terms are used. In order to provide a clear and consistent understanding of the specification and claims, the following definitions are provided.

The use of the terms "a," "an." and "the," and similar referents in the context of describing the disclosure (especially in the context of the claims) are to be construed to cover both the singular and the plural, unless otherwise indicated or clearly contradicted by the context. The terms "comprising," "having," "including." and "containing" are to be construed as open-ended terms (i.e., meaning "including, but not limited to,") unless otherwise noted. Recitation of ranges of values are merely intended to serve as a shorthand method of referring individually to each separate value falling within the range, unless otherwise indicated, and each separate value is incorporated into the specification as if it were individually recited. For example, if the range 10-15 is disclosed, then 10, 11, 12, 13, 14 and 15 are disclosed. All methods described herein can be performed in any suitable order unless otherwise indicated or clearly contradicted by context. The use of any and all examples, or exemplary language (e.g., "such as") is intended merely to better illustrate the disclosure and does not pose a limitation on the scope of the disclosure unless otherwise claimed. No language in the specification should be construed as indicating any non-claimed element as essential to the practice of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

Allele: The allele is any of one or more alternative form of a gene, all of which alleles relates to one trait or characteristic. In a diploid cell or organism, the two alleles of a given gene occupy corresponding loci on a pair of homologous chromosomes.

Anthracnose: A seedling disease caused by the pathogen *Colletotrichum lindemuthianum* L. Symptoms include dark brown to black sunken lesions on the cotyledons and stems. Severely infected cotyledons senesce prematurely, and growth of the plant is stunted. Diseased areas may girdle the stem and kill the seedling. Also known as Fungus Bean Anthracnose.

Backcrossing: Backcrossing is a process in which a breeder repeatedly crosses hybrid progeny back to one of the parents, for example, a first generation hybrid $F_1$ with one of the parental genotype of the $F_1$ hybrid.

Bacterial brown spot: A bean disease caused by the pathogen *Pseudomonas syringae* pv. *syringae*. Symptoms include small water-soaked spots that develop into distinctive necrotic brown spots about 3-8 mm in diameter on the pods, often with a narrow, diffuse yellow margin.

Bean Common Mosaic Virus (BCMV): An insect-transmitted disease with worldwide distribution that can lead to low quality harvest product and yield losses up to 100%. Resistance to this disease is highly desirable.

Bean rust: A defoliating bean disease caused by the pathogen Uromyces appendiculatus Symptoms include rust-colored pustules often surrounded by a chlorotic halo. The disease occurs worldwide and can destroy an entire crop if conditions are favorable.

Bean yield (tons/acre): The yield in tons/acre is the actual yield of the bean pods at harvest.

Determinate plant: A determinate plant will grow to a fixed number of nodes while an indeterminate plant continues to grow during the season.

Emergence: The rate that the seed germinates and sprouts out of the ground.

Essentially all the physiological and morphological characteristics: A plant having essentially all the physiological and morphological characteristics of another plant means a plant having the physiological and morphological characteristics, except for the characteristics derived from the converted gene, of the other plant. In certain embodiments the plant of the disclosure has all the physiological and morphological characteristics, except for certain characteristics mentioned, e.g. the characteristic(s) derived from a converted or introduced gene or trait and/or except for the characteristics which differ.

Field holding ability: A bean plant that has field holding ability means a plant having pods that remain smooth and retain their color even after the seed is almost fully developed.

Fruit: A ripened ovary, together with any other structures that ripen with the ovary and form a unit. In garden bean, the fruit is the pod while the seed is the bean.

Immunity to disease(s) and/or insect(s): A bean plant which is not subject to attack or infection by specific disease(s) and or insect(s) is considered immune.

Intermediate resistance to disease(s) and/or insect(s). A bean plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant bean plants are not immune to the disease(s) and or insect(s).

Machine or mechanical harvest: A machine harvestable plant means a bean plant from which the pods can be removed from the plant using one of several commercial mechanical harvesters in such a manner as to reduce the amount of broken pods, clusters, and extraneous plant matter harvested with the desired pods.

Maturity: A maturity under 53 days is considered early, while a maturity between 54-59 days is considered average or medium, and a maturity of 60 or more days would be late.

Maturity date: Plants are considered mature when the pods have reached their maximum allowable seed size and sieve size for the specific use intended. This can vary for each end user. e.g., processing at different stages of maturity would be required for different types of consumer beans, such as "whole pack." "cut." or "French style" The number of days is calculated from a relative planting date which depends on day length, heat units, and other environmental factors.

Plant adaptability: A plant having good plant adaptability means a plant that will perform well in different growing conditions and seasons.

Plant architecture: Plant architecture is the shape of the overall plant which can be tall-narrow, short-wide, medium height, and/or medium width.

Plant habit: A plant can be erect (upright) to sprawling on the ground.

Plant height: Plant height is taken from the top of the soil to the top node of the plant and is measured in centimeters or inches.

Plant part: A plant part means any part of a plant including, for example, a cell, protoplast, embryo, pollen, ovule, flower, leaf, stem, cotyledon, hypocotyl, meristematic cell, root, root tip, pistil, anther, shoot tip, shoot, fruit and petiole.

Pod position: The pod set height is the location of the pods within the plant. The pods can be high (near the top), low (near the bottom), or medium (in the middle) of the plant QTL Quantitative Trait Loci (QTL): Quantitative trait loci refer to genetic loci that control to some degree numerically representable traits that are usually continuously distributed.

Regeneration: Regeneration refers to the development of a plant from tissue culture.

Resistance to disease(s) and/or insect(s): A bean plant that restricts the growth and development of specific disease(s) and or insect(s) under normal disease(s) and or insect(s) attack pressure when compared to susceptible plants. These bean plants can exhibit some symptoms or damage under heavy disease(s) and or insect(s) pressure. Resistant bean plants are not immune to the disease(s) and or insect(s).

Seed development: The rate at which seeds develop as pods reach their harvest diameter. A slow seed development characteristic will give a cultivar its field holding ability, and a larger harvest window.

Sieve size (sv): Sieve size 1 means pods that fall through a sieve grader which culls out pod diameters of 4.76 mm through 5.76 mm Sieve size 2 means pods that fall through a sieve grader which culls out pod diameters of 5.76 mm through 7.34 mm. Sieve size 3 means pods that fall through a sieve grader which culls out pod diameters of 7.34 mm through 8.34 mm Sieve size 4 means pods that fall through a sieve grader which culls out pod diameters of 8.34 mm through 9.53 mm. Sieve size 5 means pods that fall through a sieve grader which culls out pod diameters of 9.53 mm through 10.72 mm. Sieve size 6 means pods that fall through a sieve grader that will cull out pod diameters of 10.72 mm or larger.

Single gene converted: Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Susceptible to disease(s) and or insect(s): A bean plant that is susceptible to disease(s) and or insect(s) is defined as a bean plant that has the inability to restrict the growth and development of specific disease(s) and or insect(s). Plants that are susceptible will show damage when infected and are more likely to have heavy damage under moderate levels of specific disease(s) and or insect(s).

Vegetative propagation: Means taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

A plant having "all the physiological and morphological characteristics" of a referred-to-plant means a plant having the physiological and morphological characteristics of the referred-to-plant when grown under the same environmental conditions; the referred-to-plant can be a plant from which it was derived. e.g. the progenitor plant, the parent, the recurrent parent, the plant used for tissue- or cell culture, etc. A physiological or morphological characteristic can be a numerical characteristic or a non-numerical characteristic. Physiological and morphological characteristics or traits are commonly evaluated at a significance level of 1%, 5% or 10%, when measured in plants grown under the same environmental conditions.

Similarity between different plants is defined as the number of distinguishing characteristics (or the characteristics as listed in Table 1 and/or Table 2 and/or Table 3) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

"Significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Alternatively, "significance" or "statistical significance" of differences can be expressed as a p-value. A p-value represents the probability of obtaining a result equal to or more extreme than the result actually observed. ANOVA is a suitable method for determining the value of p (Clewer. A. G., and D. H. Scarisbrick. 2001). Thus, physiological and morphological characteristics or traits are commonly evaluated at a significance level of p≤0.1, p≤0.05 or even p≤0.01 when measured in plants grown under the same environmental conditions. For example, a progeny plant of 'Lunar' may have one or more (or all) of the physiological and/or morphological characteristics of 'Lunar' listed in Table 1 and/or Table 2 and/or Table 3, as determined at the 5% significance level when grown under the same environmental conditions.

II. Overview of Garden Bean Variety 'Lunar'

Described herein is a new and distinct garden bean variety designated 'Lunar', which has superior characteristics. Garden bean variety 'Lunar' is 4 sieve garden bean variety bred for the fresh and processing market. Key selection criteria used to select 'Lunar' include concentrated setting, heat tolerance, compact, erect plant habit, and resistance to Rust and Anthracnose. In large scale trials. 'Lunar' has shown good heat tolerance Leaves of 'Lunar' are dark green. Pods are dark green. 'Lunar' is resistant to several races of the fungi anthracnose (*Colletotrichum lindemuthianum*) and Rust (*Uromyces appendiculatus*).

Garden bean variety 'Lunar' is uniform and stable within commercially acceptable limits. As is true with other garden bean varieties, a small percentage of variants can occur within commercially acceptable limits for almost any characteristic during the course of repeated multiplication.

III. Physiological and Morphological Characteristics of Garden Bean Variety 'Lunar'

In accordance with one aspect of the present disclosure, there is provided a plant having the physiological and morphological characteristics of garden bean variety 'Lunar' as presented in Table 1.

TABLE 1

Physiological and Morphological Characteristics of Garden Bean Variety 'Lunar'

| Characteristic | 'Lunar' |
|---|---|
| Market Maturity | |
| Days to Edible Pods (from planting date) | 56 |
| Market Maturity | 3 days later than comparative variety 'PV-857' |
| Plant | |
| Growth Habit | Determinate |
| Bush Form | Medium |
| Height | 43 cm |
| Spread | 40 cm |
| Pod Position | High |
| Leaves | |
| Surface Appearance | Intermediate |
| Size | Medium-Large |
| Color | Medium Dark Green |
| Anthocyanin Pigment | |
| Flowers | Absent |
| Stems | Absent |
| Pods | Absent |
| Seeds | Absent |
| Leaves | Absent |
| Petioles | Absent |
| Peduncles | Absent |
| Nodes | Absent |
| Flower Color | |
| Color of Standard | White |
| Color of Wings | White |
| Color of Keel | White |
| Pods (at Edible Maturity) | |
| Exterior Color When Fresh | Dark Green |
| Cross Section Pod Shape (at middle of pod) | Round |
| Crease Back | Absent |
| Pubescence | None-Sparse |
| Constriction (Interlocular Cavitation) | Slight |
| Spur Length | 12 mm |
| Fiber | Sparse |
| Number of Seeds/Pod | 6 |
| Suture String | Absent |
| Seed Development | Medium |
| Machine Harvest | Adapted |
| Distribution of Sieve Size at Optimum Maturity for Not-Flat Pods | 15% at Sieve Size 3 (7.34-8.34 mm) 75% at Sieve Size 4 (8.34-9.53 mm) 10% at Sieve Size 5 (9.53-10.72 mm) |
| Seed Color | |
| Seed Coat Luster | Semi-Shiny |
| Seed Coat | Monochrome |
| Primary Color | White |
| Seed Coat Pattern | Solid |
| Hilar Ring | Absent |
| Seed Shape and Size | |
| Hilum View | Elliptical |
| Cross Section | Round |

TABLE 1-continued

Physiological and Morphological Characteristics of Garden Bean Variety 'Lunar'

| Characteristic | 'Lunar' |
|---|---|
| Side View | Oval to Oblong |
| Seed Weight (g per 100 seeds) | 22 g |
| Disease Resistance | |
| Anthracnose (*Colletotrichum lindemuthianum* race 55 (lambda)) | Resistant |
| Bean Rust (*Uromyces appendiculatus* race 41) | Resistant |
| Bean Rust (*Uromyces appendiculatus* race 49) | Resistant |
| Bacterial Brown Spot (*Pseudomonas syringae* pv. *syringae*) | Not Tested |
| Halo Blight (*Pseudomonas syringae* pv. *phaseolicola* race 2) | Susceptible |
| Bean Common Mosaic Virus (BCMV) strain NL-5 | Resistant |

Comparison to Other Garden Bean Varieties

Garden bean variety 'Lunar' most closely resembles garden bean variety 'PV-857' (U.S. Pat. No. 10,390,514). 'Lunar' has pods with a significant less thick pods than the most similar variety 'PV-857' (Table 2) and also has a significantly sturdier plant than 'PV-857' (Table 3).

TABLE 2

Showing 'Lunar' has significantly thinner pods than 'PV-857' Average Pod Diameter over all available data over the years, PV857 vs. Lunar,

| Source | # of entries | Average pod diameter (mm) | F-test | T-test |
|---|---|---|---|---|
| PV857 | 42 | 10.2 | 0.33 | 6.97E−06 |
| Lunar | 9 | 9.22 | | |

F-test is used for testing the differences in the variance between the samples, this showed that the variances are equal between the two samples.
A two-sided students t-test is used to test the statistical differences between the pod diameter of PV857 and Lunar.
It is shown that the pod diameter of Lunar is very significantly lower, when compared to the pod diameter of PV857 over multiple trailing years.

TABLE 3

Showing Lunar has a significantly sturdier plant than 'PV-857' Average Plant Sturdiness (scale 1-9) over all available data over the years, PV857 vs. Lunar,

| Source | # of entries | Average Plant Sturdiness (scale 1-9) | F-test | T-test |
|---|---|---|---|---|
| PV857 | 78 | 6.26 | 0.67 | 2.34E−06 |
| Lunar | 27 | 7.41 | | |

Plant sturdiness is scored on a scale of 1-9, with 1 being non-sturdy plant and 9 being a very sturdy plant.
F-test is used for testing the differences in the variance between the samples, this showed that the variances are equal between the two samples.
A two-sided students t-test is used to test the statistical differences between the plant sturdiness of PV857 and Lunar.
It is shown that the plant of Lunar is significantly sturdier, when compared to the plant of PV857 over multiple trailing years.

IV. Further Embodiments

Gene Conversions

When the term "garden bean plant" is used in the context of the present disclosure, this also includes any gene conversions of that variety. The term "gene converted plant" as used herein refers to those garden bean plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present disclosure to improve or introduce a characteristic into the variety. The term "backcrossing" as used herein refers to the repeated crossing of a hybrid progeny back to the recurrent parent. i.e., backcrossing 1, 2, 3, 4, 5, 6, 7, 8, 9, or more times to the recurrent parent. The parental garden bean plant which contributes the gene for the desired characteristic is termed the "nonrecurrent" or "donor parent." This terminology refers to the fact that the nonrecurrent parent is used one time in the backcross protocol and therefore does not recur. The parental garden bean plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a garden bean plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus.

Tissue Culture

Further reproduction of the variety can occur by tissue culture and regeneration. Tissue culture of various tissues of garden bean and regeneration of plants therefrom is well known and widely described. For example, reference may be made to McClean et al., *Plant Sci.* 60.117-122, 1989; Mergeai et al., *B.I.C. Invit. Papers.* 33.115-116, 1990; Vanderwesthuizen et al., *S. Aft. J. Bot.* 56:271-273, 1990; Benedicic et al., *Abst. 5th I.A.P.T.C. Cong.* 1:91 (#A3-33), 1990; Franklin et al., *Plant Cell Tissue Org. Cult.* 24:199-

206, 1991; Malik et al., *Planta.* 184.148-150, 1991; Malik et al., *Planta.* 186:384-389, 1992; Lewis et al., *J. Am. Soc. Hort. Sci.,* 119-361, 1994; and Song et al., *J. Plant Physiol.* 146:148-154, 1995. It is clear from the literature that the state of the art is such that these methods of obtaining plants are routinely used and have a very high rate of success. Thus, another aspect of this disclosure is to provide cells which upon growth and differentiation produce garden bean plants having the physiological and morphological characteristics of variety 'Lunar' when evaluated at significance levels of 1%, 5%, or 10% significance.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. The cells of the tissue culture of the current disclosure may be produced from any suitable plant part of garden bean variety 'Lunar'. In some embodiments, the cells of the tissue culture are produced from a plant part selected from the group consisting of embryos, meristematic cells, leaves, pollen, roots, root tips, stems, anthers, pistils, pods, flowers, and seeds.

Transgenic Plants

In some aspects, the present disclosure provides methods for producing a transgenic garden bean plant comprising transforming a plant of garden bean variety 'Lunar' with a transgene that confers a trait.

As used herein, the term "transgene" refers to a nucleic acid molecule artificially incorporated into a host cell's genome. Such transgene may be heterologous to the host cell. As used herein, the term "heterologous" refers to a sequence which is not normally present in a given host genome in the genetic context in which the sequence is currently found. In this respect, the sequence may be native to the host genome, but be rearranged with respect to other genetic sequences within the host sequence. The term "transgenic plant" refers to a plant comprising such a transgene or part thereof. A "transgenic plant" includes a plant, plant part, a plant cell or seed whose genome has been altered by the integration of such a transgene or part thereof. A transgenic plant includes a plant regenerated from an originally-transformed plant cell and progeny transgenic plants from later generations or crosses of a transformed plant.

As used herein, the term "transformation" and "transforming" a plant cell encompasses all techniques by which a nucleic acid molecule may be introduced into such a cell. Examples include, but are not limited to: transfection with viral vectors; transformation with plasmid vectors, electroporation, microinjection; *Agrobacterium*-mediated transfer; direct DNA uptake; Whiskers-mediated transformation, and microprojectile bombardment Methods of plant transformation are well known in the art. For example, reference may be made to Draper et al., *Blackwell Sci. Pub. Oxford,* p. 365, 1988; Potrykus and Spangenburg. Springer-Verlag, 1995; and Gelvin et al., *Plant Mol. Biol. Manual.* 1993. A review of transgenic plants, including transformation techniques, is provided in Galun and Breiman, *Transgenic Plants,* 1997. Additionally, the following representative publications disclose transformation protocols that may be used to genetically transform garden beans: Veltcheva, et al., *Sci. Hortic.* 107:2-10, 2005; Liu et al., *Mol. Breed.* 16:189-197, 2005; Brasileiro et al., *J. Am. Soc. Hortic. Sci.* 121:810-815, 1996; Zambre et al., *Theor. Appl. Genet.* 110:914-924.2005; Oldroyd et al., *Plant Physiol.* 137:1205-1210, 2005; and Estrada-Navarrete et al., *Nat Protoc.* 2(7):1819-24, 2007.

The trait may be any suitable trait known in the art including, for example, male sterility, male fertility, herbicide resistance, insect or pest (e.g., insect and/or nematode) resistance, disease resistance (e.g., for bacterial, fungal and/or viral disease), water stress tolerance, heat tolerance, salt tolerance, modified fatty acid metabolism, modified carbohydrate metabolism, improved shelf-life, improved nutritional quality, increased sweetness, increased flavor, improved ripening control, improved yield, industrial usage, or any combination thereof. In some embodiments, the trait is selected from the group consisting of herbicide resistance, insect resistance, disease resistance, and a combination thereof.

In some embodiments, the trait of herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof. In some embodiments, the herbicide is selected from the group consisting of imidazolinone, sulfonylurea, glyphosate, glufosinate, L-phosphinothricin, triazine, and benzonitrile.

In some embodiments, the trait of insect resistance is conferred by *Bacillus thuringiensis* (Bt) protein, a derivative thereof, or a synthetic polypeptide modelled thereon. See, for example. Geiser, et al., *Gene.* 48:109 (1986), which discloses the cloning and nucleotide sequence of a Bt δ-endotoxin gene. Moreover. DNA molecules encoding δ-endotoxin genes can be purchased from American Type Culture Collection. Manassas, Va., for example, under ATCC Accession Nos. 40098, 67136, 31995, and 31998.

In some embodiments, the trait of disease resistance confers resistance to anthracnose (*Colletotrichum lindemuthianum*), bean rust (*Uromyces appendiculatus*), bacterial brown spot (*Pseudomonas syringae* pv. *syringae*), halo blight (*Pseudomonas syringae* pv *phaseolicola*), bean common mosaic virus (BCMV), or any combination thereof.

In some aspects, the present disclosure provides a transgenic garden bean plant derived from garden bean variety 'Lunar' according to any of the methods described herein. In some embodiments, the transgenic garden bean plant have at least 1, 2, 3, 4, 5, 6, 7, 8, 9, 10 or more of the morphological and physiological characteristics of garden bean variety 'Lunar' (e.g., as described herein, in particular, in Section III), or even all of the morphological and physiological characteristics of garden bean variety 'Lunar', so that said plants are not significantly different for said traits than garden bean variety 'Lunar', as determined at the 5% significance level when grown in the same environmental conditions, optionally, with the presence of one or more desired additional traits (e.g., disease resistance, insect resistance, and/or herbicide resistance).

Additional Breeding Methods

The disclosure is also directed to methods for producing a garden bean plant by crossing a first parent garden bean plant with a second parent garden bean plant where the first or second parent garden bean plant is a garden bean plant of variety 'Lunar'. Further, both first and second parent garden bean plants can come from garden bean variety 'Lunar'. Thus, any such methods using garden bean variety 'Lunar' are part of the disclosure: selfing, backcrosses, hybrid production, crosses to populations, and the like. All plants produced using garden bean variety 'Lunar' as at least one parent are within the scope of this disclosure, including those developed from varieties derived from garden bean variety 'Lunar'. Advantageously, this garden bean variety could be used in crosses with other, different, garden bean plants to produce the first generation ($F_1$) garden bean hybrid seeds and plants with superior characteristics. The variety of the disclosure can also be used for transformation where exogenous genes are introduced and expressed by the variety of the disclosure. Genetic variants created either through traditional breeding methods using garden bean variety 'Lunar', or through transformation of variety 'Lunar' by any of a number of protocols known to those of skill in the art are intended to be within the scope of this disclosure.

The following describes breeding methods that may be used with garden bean variety 'Lunar' in the development of further garden bean plants. One such embodiment is a method for developing variety 'Lunar' progeny garden bean plants in a garden bean plant breeding program, by: obtaining the garden bean plant, or a part thereof, of variety 'Lunar', utilizing said plant or plant part as a source of breeding material, and selecting a garden bean variety 'Lunar' progeny plant with molecular markers in common with variety 'Lunar' and/or with morphological and/or physiological characteristics of variety 'Lunar'. The morphological and physiological characteristics of ' Lunar' are provided in Table 1 and/or Table 2 and/or Table 3. Breeding steps that may be used in the garden bean plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized. Encompassed herein are also plants derivable from 'Lunar' (e.g. by selfings and/or crossing and/or backcrossing with 'Lunar' and/or progeny thereof) comprising all the physiological and morphological characteristics of 'Lunar' listed in Table 1 and/or Table 2 and/or Table 3 as determined at the 5% significance level for numerical characteristics or identical for non-numerical characteristics when grown under the same environmental conditions.

Another method involves producing a population of garden bean variety 'Lunar' progeny garden bean plants, by crossing variety 'Lunar' with another garden bean plant, thereby producing a population of garden bean plants, which, on average, derive 50% of their alleles from garden bean variety 'Lunar'. A plant of this population may be selected and repeatedly selfed or sibbed with a garden bean variety resulting from these successive filial generations. One embodiment of this disclosure is the garden bean variety produced by this method and that has obtained at least 50% of its alleles from garden bean variety 'Lunar'. One of ordinary skill in the art of plant breeding would know how to evaluate the traits of two plant varieties to determine if there is no significant difference between the two traits expressed by those varieties (see, e.g., Fehr and Walt, *Principles of Variety Development*, pp. 261-286, 1987). Thus the disclosure includes garden bean variety 'Lunar' progeny garden bean plants containing a combination of at least two variety 'Lunar' traits described above, so that said progeny garden bean plant is not significantly different for said traits than garden bean variety 'Lunar' as determined at the 5% significance level when grown in the same environmental conditions. Using techniques described herein, molecular markers may be used to identify said progeny plant as a garden bean variety 'Lunar' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

In other embodiments of the disclosure, garden bean variety 'Lunar' may be crossed with itself or with any second plant. Such methods can be used for propagation of 'Lunar' or can be used to produce plants that are derived from 'Lunar' Plants derived from garden bean variety 'Lunar' may be used, in certain embodiments, for the development of new garden bean varieties.

The development of new varieties using one or more starting varieties is well known in the art. In accordance with the disclosure, novel varieties may be created by crossing garden bean variety 'Lunar' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination Once initial crosses have been made, inbreeding and selection take place to produce new varieties. For development of a uniform line, often five or more generations of selfing and selection are involved.

Progeny of garden bean variety 'Lunar' may also be characterized through their filial relationship with garden bean variety 'Lunar', as for example, being within a certain number of breeding crosses of garden bean variety 'Lunar'. A breeding cross is a cross made to introduce new genetics into the progeny, and is distinguished from a cross, such as a self or a sib cross, made to select among existing genetic alleles. The lower the number of breeding crosses in the pedigree, the closer the relationship between garden bean variety 'Lunar' and its progeny. For example, progeny produced by the methods described herein may be within 1, 2, 3, 4, or 5 breeding crosses of garden bean variety 'Lunar'.

Trait Introduction

When using a transgene, the trait is generally not incorporated into each newly developed variety, such as garden bean variety 'Lunar', by direct transformation. Rather, the more typical method used by breeders of ordinary skill in the art to incorporate the transgene is to take a variety already carrying the transgene and to use such variety as a donor to transfer the transgene into the newly developed line by backcrossing. The same would apply for a naturally occurring trait or one arising from spontaneous or induced mutations. As used herein, the term "backcrossing" refers to a process in which a breeder repeatedly crosses hybrid progeny back to one of the parents, for example, a first generation hybrid $F_1$ with one of the parental genotype of the $F_1$ hybrid. Accordingly, in some embodiments, the present disclosure provides a method for introducing a trait into garden bean variety 'Lunar', the method comprising: (a) crossing a plant of garden bean variety 'Lunar' with another garden bean plant that comprises a trait to produce $F_1$ progeny plants, wherein the trait is selected from the group consisting of insect resistance, disease resistance, water stress tolerance, heat tolerance, improved shelf-life, improved nutritional quality, improved yield, and a combination thereof; (b) selecting one or more progeny plants that have the trait to produce selected progeny plants, (c) backcrossing the selected progeny plants with plants of garden bean variety 'Lunar' to produce backcross progeny plants; (d) selecting for backcross progeny plants that have the trait; and (e)

repeating steps (c) and (d) one or more times to produce further backcross progeny plants that have the trait.

The trait may be any suitable trait known in the art including, for example, male sterility, male fertility, herbicide resistance, insect or pest (e.g., insect and/or nematode) resistance, disease resistance (e.g., for bacterial, fungal and/or viral disease), water stress tolerance, heat tolerance, salt tolerance, modified fatty acid metabolism, modified carbohydrate metabolism, improved shelf-life, improved nutritional quality, increased sweetness, increased flavor, improved ripening control, improved yield, industrial usage, or any combination thereof. In some embodiments, the trait is a naturally occurring one. In some embodiments, the trait is a transgenic one. In some embodiments, the trait is selected from the group consisting of insect resistance, disease resistance, water stress tolerance, heat tolerance, improved shelf-life, improved nutritional quality, improved yield, and a combination thereof.

V. Deposit Information

A deposit of the garden bean variety 'Lunar' (Breeder's designation 'PV-959') is maintained by Pop Vriend Seeds B.V., having an address at Middenweg 52, P.O. Box 5, 1619 ZG Andijk, the Netherlands. Access to this deposit will be available during the pendency of this application to persons determined by the Commissioner of Patents and Trademarks to be entitled thereto wider 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building. Craibstone Estate, Bucksburn, Aberdeen, AB21 9YA, United Kingdom.

At least 2500 seeds of garden bean variety 'Lunar' (Breeder's designation 'PV-959') were deposited on Jul. 27, 2022, according to the Budapest Treaty in the National Collection of Industrial, Food and Marine Bacteria Ltd (NCIMB Ltd), Ferguson Building, Craibstone Estate. Bucksburn, Aberdeen. AB21 9YA, United Kingdom. The deposit has been assigned NCIMB Accession No. 44005. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed. The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A seed of garden bean variety designated 'Lunar', wherein a representative sample of seed of the variety has been deposited under NCIMB Accession No. 44005.

2. A garden bean plant produced by growing the seed of claim 1.

3. A plant part from the plant of claim 2.

4. The plant part of claim 3, wherein the part is a leaf, a pod, a garden bean hull, a garden bean, a stem, a root, or a flower.

5. A tissue culture of regenerable cells produced from the plant of claim 2.

6. A garden bean plant regenerated from the tissue culture of claim 5, wherein the plant has all of the physiological and morphological characteristics of garden bean variety 'Lunar' when the characteristics are determined at the 5% significance level for numerical characteristics or are identical for non-numerical characteristics and when grown under the same environmental conditions.

7. A method for producing a hybrid garden bean seed, comprising crossing a first parent garden bean plant with a second parent garden bean plant and harvesting the resultant hybrid garden bean seed, wherein the first parent garden bean plant or the second parent garden bean plant is the plant of claim 2.

8. An $F_1$ hybrid garden bean seed produced by the method of claim 7.

9. A method for producing a transgenic garden bean plant, comprising transforming the plant of claim 2 with a transgene that confers a trait.

10. The method of claim 9, wherein the trait is selected from the group consisting of herbicide resistance, insect resistance, disease resistance, and a combination thereof.

11. The method of claim 10, wherein the trait is herbicide resistance and the herbicide is selected from the group consisting of imidazolinone, sulfonylurea, glyphosate, glufosinate, L-phosphinothricin, triazine, and benzonitrile.

12. The method of claim 10, wherein the trait is insect resistance and the insect resistance is conferred by a transgene encoding a *Bacillus thuringiensis* endotoxin.

13. A transgenic garden bean plant, or a plant part thereof, produced by the method of claim 9.

14. A method for introducing a trait into garden bean variety 'Lunar', the method comprising: (a) crossing a plant of garden bean variety 'Lunar', wherein a representative sample of seed of the variety has been deposited under NCIMB Accession No. 44005, with another garden bean plant that comprises a trait to produce F1 progeny plants, wherein the trait is selected from the group consisting of insect resistance, disease resistance, water stress tolerance, heat tolerance, improved shelf-life, improved nutritional quality, improved yield, and a combination thereof; (b) selecting one or more progeny plants that have the trait to produce selected progeny plants; (c) backcrossing the selected progeny plants with plants of garden bean variety 'Lunar' to produce backcross progeny plants; (d) selecting for backcross progeny plants that have the trait; and (e) repeating steps (c) and (d) one or more times to produce further backcross progeny plants that have the trait.

15. A garden bean plant, or a plant part thereof, produced by the method of claim 14, wherein the plant has the trait and otherwise has all of the physiological and morphological characteristics of garden bean variety 'Lunar' when determined at the 5% significance level.

16. The garden bean plant of claim 15, wherein the trait is herbicide resistance and the herbicide is selected from the group consisting of imidazolinone, sulfonylurea, glyphosate, glufosinate, L-phosphinothricin, triazine, and benzonitrile.

17. The garden bean plant of claim 15, wherein the trait is insect resistance and the insect resistance is conferred by a transgene encoding a *Bacillus thuringiensis* endotoxin.

18. A method for producing a garden bean pod, comprising: (a) cultivating the plant of claim 2 to produce a garden bean pod; and (b) harvesting the garden bean pod.

19. The garden bean pod produced by the method of claim 18.

20. A method of producing a seed of a 'Lunar' derived garden bean plant, the method comprising the steps of:

(a) producing a 'Lunar' derived garden bean plant from a seed produced by crossing the garden bean plant of claim 2 with itself or with a second garden bean plant; and (b) crossing the 'Lunar' derived garden bean plant with itself or a different garden bean plant to obtain a seed of a further 'Lunar' derived garden bean plant.

21. The method of claim 20, further comprising producing a garden bean plant grown from the seed of said step (b) and crossing said garden bean plant with itself or a different garden bean plant to produce a seed of a further 'Lunar' derived garden bean plant.

22. A garden bean plant wherein the plant has all of the physiological and morphological characteristics of the plant of claim 2 when the characteristics are determined at the 5% significance level for numerical characteristics and are identical for non-numerical characteristics and when grown under the same environmental conditions.

23. A plant part from the plant of claim 22.

24. The plant part of claim 23, wherein the part is a leaf, a pod, a garden bean hull, a garden bean, a stem, a root, or a flower.

\* \* \* \* \*